US008600771B2

(12) United States Patent
Mahesh et al.

(10) Patent No.: US 8,600,771 B2
(45) Date of Patent: Dec. 3, 2013

(54) SYSTEMS AND METHODS FOR GENERATING A TEACHING FILE MESSAGE

(75) Inventors: Prakash Mahesh, Hoffman Estates, IL (US); Murali Kariathungal, Hoffman Estates, IL (US); Jeffrey James Whipple, Severn, MD (US); Khan Siddiqui, Timonium, MD (US)

(73) Assignee: General Electric Company, Schenectady, NY (US)

( * ) Notice: Subject to any disclaimer, the term of this patent is extended or adjusted under 35 U.S.C. 154(b) by 1531 days.

(21) Appl. No.: 11/943,844

(22) Filed: Nov. 21, 2007

(65) Prior Publication Data
US 2009/0130641 A1 May 21, 2009

(51) Int. Cl.
*G06Q 50/00* (2012.01)
(52) U.S. Cl.
USPC .............................................................. 705/2
(58) Field of Classification Search
USPC ............................................................ 705/2–3
See application file for complete search history.

(56) References Cited

U.S. PATENT DOCUMENTS

| 7,047,235 | B2 | 5/2006 | Yang et al. | |
|---|---|---|---|---|
| 2003/0208477 | A1* | 11/2003 | Smirniotopoulos et al. | 707/3 |
| 2004/0107210 | A1* | 6/2004 | Yang et al. | 707/104.1 |
| 2004/0236791 | A1* | 11/2004 | Kinjo | 707/104.1 |
| 2005/0202382 | A1* | 9/2005 | Rahn et al. | 434/262 |
| 2006/0083442 | A1* | 4/2006 | Loukipoudis et al. | 382/305 |
| 2007/0061393 | A1* | 3/2007 | Moore | 709/201 |
| 2007/0118550 | A1* | 5/2007 | Yang et al. | 707/102 |
| 2008/0040151 | A1* | 2/2008 | Moore | 705/2 |
| 2009/0222406 | A1* | 9/2009 | Allred et al. | 707/2 |
| 2009/0274384 | A1* | 11/2009 | Jakobovits | 382/254 |

OTHER PUBLICATIONS

MexPix, Web Archive (www.archive.org) of MedPix website (rad.usuhs.mil) on Oct. 25, 2000.*
ACC, HIMSS and RSNA. "IHE Radiology Technical Framework Supplement 2004-2005: Teaching File and Clinical trial Export (TCE)", accessed on Jul. 27, 2011 via www.archive.org at http://web.archive.org/web/20060515061012/http://www.ihe.net/Technical_Framework/upload/IHE_TF_Suppl_Teaching_File_Clinical_Trial_Export_TI_2005-04-22.pdf. Apr. 22, 2005.*
Whipple, Lau, Siddiqui, Juluru, Perry, Beaulieu, Herfkens, Siegel; Demonstration of the New IHE Teaching File and Clinical Trials Export Profile with a MIRC Toolset, RSNA06 Exhibit LL-IN3049 (Poster), 2006, U.S.

* cited by examiner

*Primary Examiner* — Luke Gilligan
*Assistant Examiner* — Robert Sorey
(74) *Attorney, Agent, or Firm* — Hanley, Flight and Zimmerman, LLC

(57) ABSTRACT

Certain embodiments present a system for generating a medical teaching file message. An image identifier labels medical images based upon information pertaining to user interaction with the image. The system also provides an image search engine that scans and indexes images within a database based on a set of rules. The image search engine generates a subset of images from a larger group of medical images within a database based upon the rules. The system also includes a supporting data selection engine for accepting a free text search query from an interface. The supporting data selection engine scans medical databases based on the free text search query, and provides the supporting data search results via an interface. A teaching file message is generated either automatically or manually from the subset of images and the supporting data search results for transmission to a teaching file.

10 Claims, 6 Drawing Sheets

SYSTEMS AND METHODS FOR GENERATING A TEACHING FILE MESSAGE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Certain embodiments of the present technology relate to generation of teaching files from healthcare information systems. More particularly, certain embodiments relate to methods and systems for automatically selecting potential teaching file images and using a search engine to produce supporting data.

In medical environments, teaching is often linked with diagnosis and treatment. For example, a medical practitioner will often generate information to be included in a medical teaching file while reviewing images, such as radiology scans, where the practitioner believes the images can be useful in teaching a particular medical subject matter. The generation of these teaching files can be important building blocks for clinical support, teaching and research.

The process for generation of a teaching file is often initiated by a medical practitioner. The practitioner will assemble a package of images and data, also known as a teaching file message, and providing the message to a user that will create a teaching file using the information in the teaching file message. The teaching file message is generally comprised of medical images, and supporting data such as reports, graphics and other information helping to portray and explain the subject matter at hand. The duties of a medical practitioner in the generation of a teaching file therefore generally involve selecting medical images, and searching for, or generating the supporting data.

In prior methods of non-electronic teaching file generation, a practitioner reviewing film would take certain images that the practitioner deemed appropriate and copy the images into a paper folder with accompanying notes. However, as medical imaging technology moved into a digital environment, the teaching file creation process began to adapt. In digital environments such as a Picture Archiving and Communication Systems (PACS), images may be manipulated and cross-referenced in a powerful and interactive fashion. A PACS is a clinical image archive system and may comprise a series of computers or networks dedicated to the storage, retrieval, distribution and presentation of images. The medical images are stored in an independent format. As more hospitals adopt PACS, a scalable repository of case-based files will become a valuable tool for on-demand learning and exchange of data. Teaching files may be created by compiling a series of medical images, such as radiological scans, and adding data, text, graphics, charts or other information to serve as a reference guide for future users.

To assist in adapting to the newer technological environments, the Integrating the Healthcare Enterprise (IHE) initiative was established. The IHE is an initiative by healthcare organizations and vendors, supported by the Radiological Society of North America (RSNA) to improve the way computer systems in healthcare share information. One of the achievements of the IHE pertaining to the creation of teaching files is the establishment of a Teaching File and Clinical Trial Export (TCE) profile. IHE-TCE defines standards for gathering together teaching file images and related information for automatic routing to teaching file servers. For example, the process of generating a teaching file from a teaching file message is an artifact of the IHE-TCE profile. However, the IHE-TCE profile leaves the tasks of initial image selection and data entry as a manual processes to be performed by the radiologist. For example, a radiologist is to review each image, flagging images the radiologist deems appropriate for the teaching file, and further entering data or other information.

Another shortcoming of present teaching file generation methods is that practitioners do not typically know the final outcome, diagnosis or pathology for a particular case at the time of interpretation. Therefore, it may take several days to complete a teaching file message under this method. Furthermore, practitioners do not always realize that a particular case is worth documenting as a teaching file during the interpretation process. When the final diagnosis or interesting information does become available, the practitioners may have to manually research back to find the case to generate a teaching file, thereby disrupting workflow.

Presently, to generate images for the teaching file message, the medical practitioner must either select images and data that are to be included in the file message either during the interpretation process (a process of interpreting or reading medical or radiological images) or a medical study or retrieve the images and data after the interpretation process is completed. Each medical study, such as a computed tomography (CT) study or a Magnetic Resonance Imaging (MRI) study, may contain hundreds or thousands of individual images, only a few of which may be valuable for use in a teaching file. Thus, in order to create a teaching file of clinical images the radiologist will have to document or remember each image deemed appropriate for teaching as it is recorded or reviewed. Such a process is burdensome and can detract from the radiologist's ultimate objectives.

Alternatively, the practitioner may spend additional time reviewing images for teaching file generation after they have already been viewed once. In either situation, the selection of images for the teaching file generation process is time consuming and burdensome on the practitioner, and leaves high room for error in both the interpretation process and in the generation of a teaching file. Thus, there exists a need to provide a system that will automatically flag and identify images in a PACS appropriate for a teaching file based on properties associated with the images.

As mentioned, medical practitioners must also generate supporting data to accompany the medical images in the teaching file messages. Supporting data may include already existing radiology report, teaching files, medical reports or other clinical information related to the subject matter of the teaching file. However, supporting data may be stored in multiple systems that are outside of the PACS, and thus be very difficult for a practitioner to efficiently retrieve. To gather this data, the practitioner must browse through each system containing the information until the desired data to accompany the images is found.

Thus, gathering data on clinical systems can be a difficult task. Current clinical or image-related systems often organize data in a format determined by developers that is unusable by one or more medical practitioners in the field. Additionally, information may be stored in a format that does not lend itself to data retrieval and usage in other contexts. These problems make the teaching file creation process difficult and time consuming, and can be disruptive the interpretation process.

An increasing number of medical information systems require free text search capability for searching finding information about a specific medical diagnosis, patient demographics, decease statistics, etc. However, these search engines are not customized for searching electronic medical records. Therefore, there is a need for systems and methods for free text searching capability with electronic medical records to obtain supporting data accompanying images in a teaching file message.

BRIEF SUMMARY OF THE INVENTION

Certain embodiments present a system for generating a medical teaching file message. Certain embodiments provide an image identifier that generates an image label to each of a group of medical images within an image database based at least in part upon the image content, or image information. The system also provides a rule based image search engine that scans and indexes images within an image database based on a set of rules. The image search engine generates a subset of medical images from a group of medical images based upon the selection engine rules. Certain embodiments include an interface for displaying the medical images. In certain embodiments, the image search engine populates the interface with the images from the image subset allowing a user to select medical images from the subset for inclusion in a medical teaching file message for transmission to a teaching file server.

Certain embodiments present a system for generating a medical teaching file message having an image identifier, a rule based image search engine, an interface, and a supporting data selection engine. The supporting data selection engine may accept a free text search query from the interface, based on search criteria entered via the interface. Certain embodiments present a search crawler in communication with the supporting data selection engine. The search crawler may search electronic medical record data based on the free text search query, and provide the supporting data search results consolidating supporting data through the free text search. In certain embodiments the image search engine and the supporting data selection engine populate the interface with the images from the image subset and the supporting data search results via the interface, allowing a user to select medical images and supporting data for inclusion in a medical teaching file message for transmission to a teaching file.

Certain embodiments present a method for automatically generating a teaching file message on a picture archiving and communication system during a medical interpretation process. The method includes recording image information for each image viewed during the medical interpretation process, generating a subset of the images viewed during the medical interpretation process according to image search rules, and receiving a supporting data search query through an interface based on one or more search terms. The method further includes crawling one or more databases associated with one or more healthcare information systems to identify relevant supporting data based on the search queries, populating an interface with the image subset and relevant supporting data. The method further includes assembling a teaching file message via the interface and transmitting the message to a teaching file server.

Figure 1:
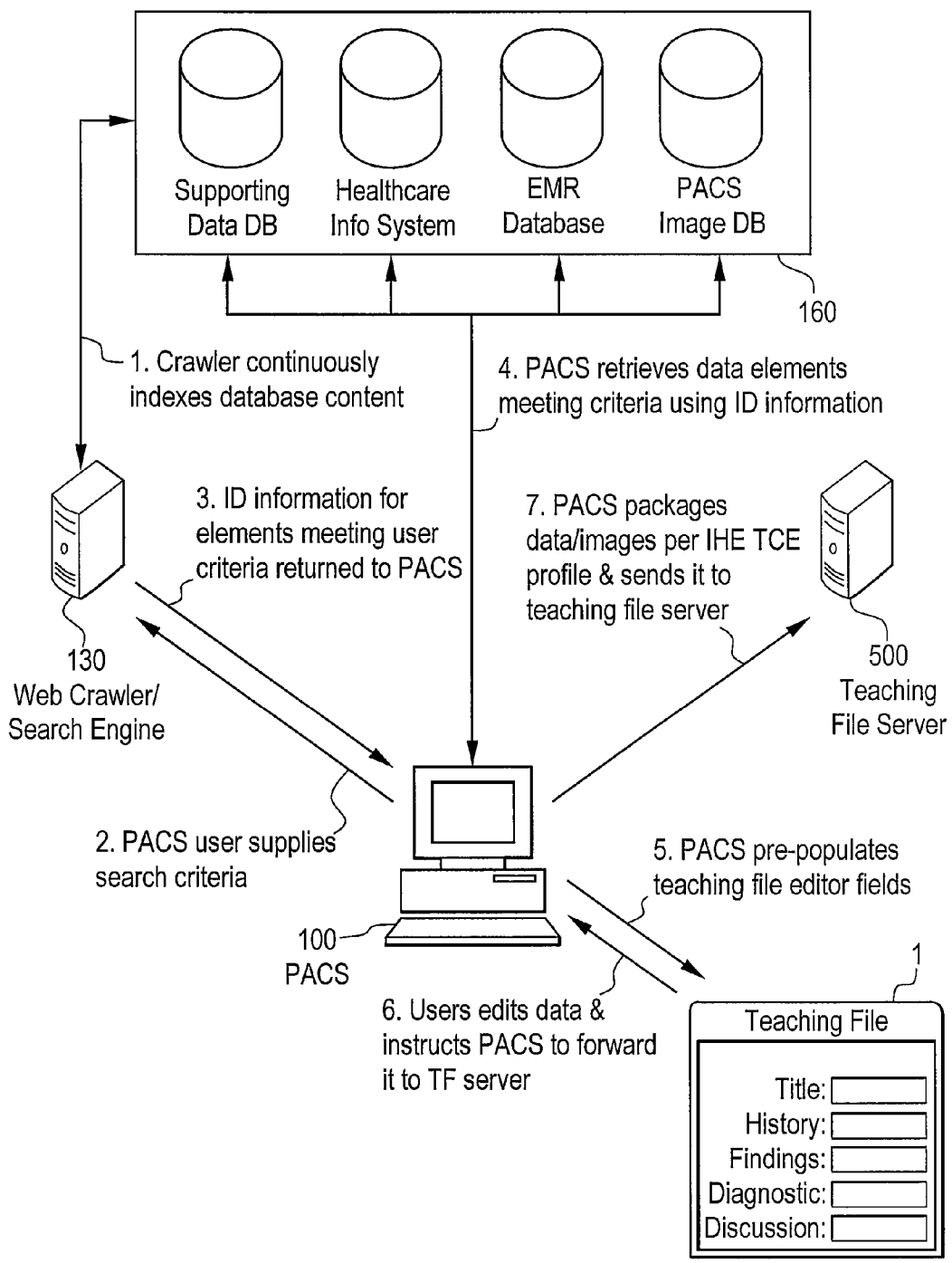
FIG. 1 illustrates an automated teaching file creation flow diagram.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide systems and methods for generating a teaching file package containing data and images, or a teaching file message, that is used to create a teaching file. For example, a medical practitioner, such as a radiologist, may desire to produce a package including data, information and images in order to generate a teaching file on a particular medical subject after conducting a study, or while reviewing and interpreting images such as radiology scans. Certain embodiments provide methods and systems for identifying a subset of potential teaching file images using an automated image selection feature driven on a set of rules. Certain embodiments also provide methods and systems for using a search engine to populate data fields generating potential teaching file supporting data.

FIG. 1 depicts and exemplary flow diagram of an automated teaching file creation process. A PACS teaching file generation system 100 is provided to interact with various databases 160 or healthcare information systems. In certain embodiments, the system may interact with only one database. In other embodiments, the system 100 may interact with multiple databases and healthcare information systems, each healthcare information system potentially having multiple databases of its own.

In certain embodiments, a web crawler, or search engine 130, interacts with both the system 100 and the databases 160 to continuously index database content. For example, data and images in the databases 160 may be continuously updated with labels identifying aspects of the data, such as information pertaining to when the data was created and how frequently the data or images are accessed by other practitioners. In the depicted embodiment the search engine 130 is exterior to the system 100, but in certain embodiments the search engine 130 may be a component of the system 100.

Whether the search engine is a component of, or separate from the system 100, a user of the system 100 supplies the search engine 130 with a search criteria. For example, the search criteria may be in the form of a search query or a set of search rules. The search engine 130 then scans the various databases 160 for information meeting the user or rule identified criteria and returns the results in the form of Identification (ID) information to the system. In certain embodiments, the ID may be in the form of a tag, or a label identifying image information provided by an image identifier that is either a part of the system 100 or the search engine 130. In certain embodiments, the system 100 then retrieves the data elements from the databases 60 using the ID information supplied by the search engine. In certain embodiments, the results of the search are then populated on the system 100 via an interface that may be accessed by a user.

In certain embodiments, a user may create, access, and/or modify a teaching file message using a teaching file editor program. In certain embodiments the teaching file editor is provided to the user via a user interface 1 at a computer workstation, for example. In certain embodiments, the system 100 pre-populates a teaching file editor fields with information withdrawn from the databases 160. The user may then edit data via the teaching file editor interface 1 and establish a teaching file message. The user may also instruct the system 100 to forward the information to a teaching file server 500. In certain embodiments, the system packages 100 data, images and other information in the assembled teaching file message in accordance with certain profiles (e.g., IHE-TCE), and then sends the teaching file message to a teaching file server 500. The teaching file creation process is completed at the teaching file server 500, where the teaching file is assembled into a finished teaching file.

Figure 2:
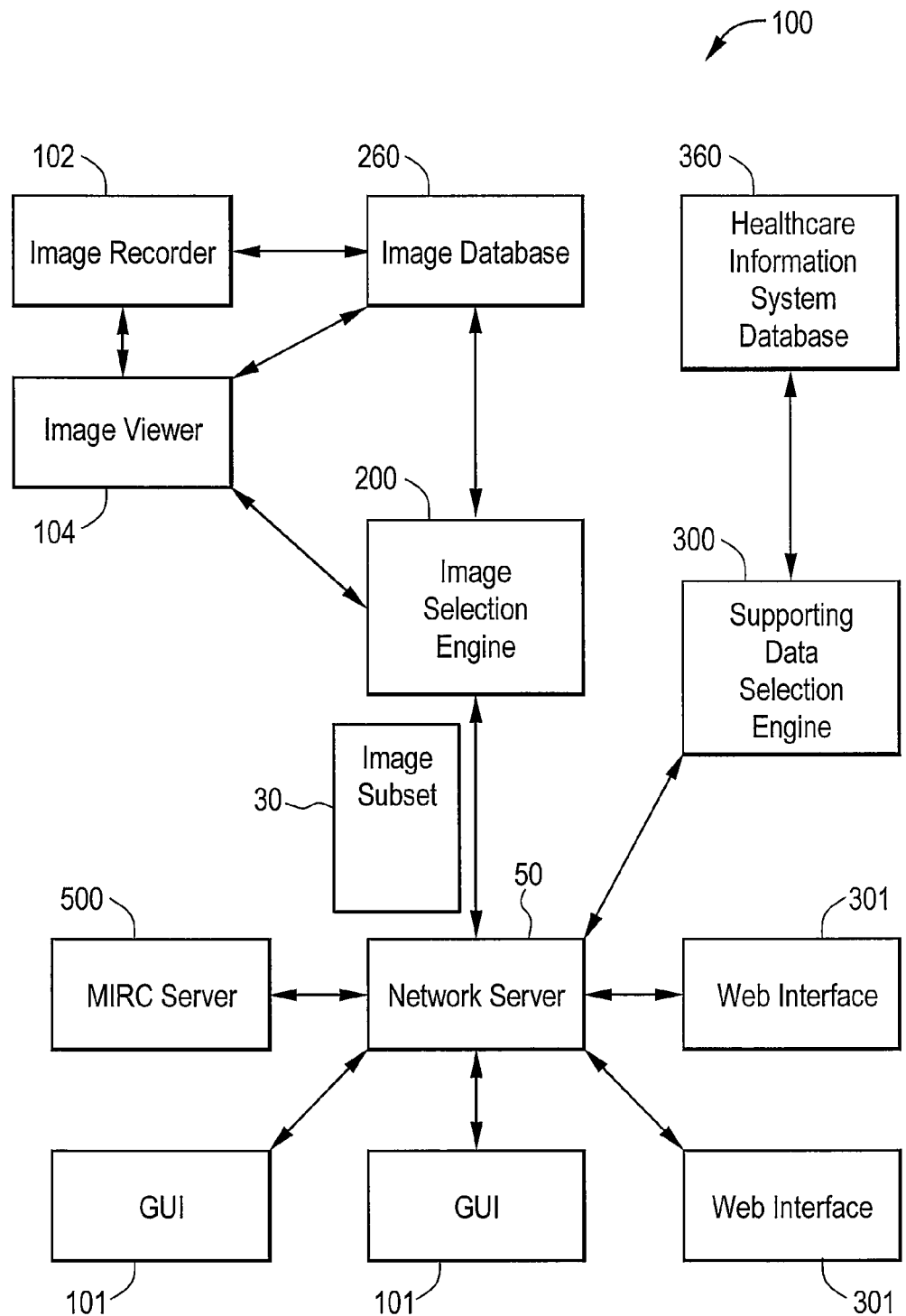
FIG. 2 illustrates a system block diagram of the components of a teaching file creation system.

FIG. 2 depicts an embodiment of a system for generating a teaching file message. In certain embodiments, the system 100 may be located within a PACS. In certain embodiments, the teaching file message generation system may be external from but in communication with PACS. For example, the teaching file message generation system may only need to interact with PACS in order to retrieve images and supporting data stored in the PACS.

In certain embodiments, a radiologist may use the teaching file message generation system 100 of FIG. 2 to generate a teaching file message during a radiological interpretation process, for example. In certain embodiments, a teaching file message generation system 100 comprises an image recorder 102 such as a radiology scanner or an x-ray scanner. A medical practitioner, for example, a radiologist, may record images using the image recorder 102 and store them within an image database 260. During the interpretation process, the medical practitioner may view and examine the images using an image viewer 104. In certain embodiments, the practitioner may view and study the recorded images as they are recorded using the image viewer 104. In certain embodiments, the image viewer 104 may be a part of a user interface such as teaching file editor 1, or a graphical user interface on a computer workstation.

In certain embodiments, the system 100 will not have an image recorder, rather the images will be produced by components external to the system and then forwarded to the PACS. For example, the teaching file message generation system 100 may not be able to access the imaging system itself, instead only having access to exams and studies sent to the system 100 by PACS.

Because studies and/or interpretations may contain several hundred or thousand images, and since most teaching file images are selected from a small subset of images focused on by the practitioner during interpretation, an automated image selection engine 200 may determine which images viewed by the practitioner should be a part of this small subset. The image selection engine 200 identifies potential images suitable for a teaching file based on a set of rules. In certain embodiments, the image selection engine 200 tracks the practitioner's interactions with each image, gathering image information or data such as image hits, image viewing time, and image processing used, for example. In certain embodiments, the image selection engine 200 is rule driven, and applies the rules to the user tracking data to identify which images are anticipated to interest the practitioner, and defines these images in an image subset 30. A user can therefore browse a much smaller directory of images in choosing the images for a teaching file message, eliminating the majority of images likely to be unsuitable for a teaching file.

Figure 3:
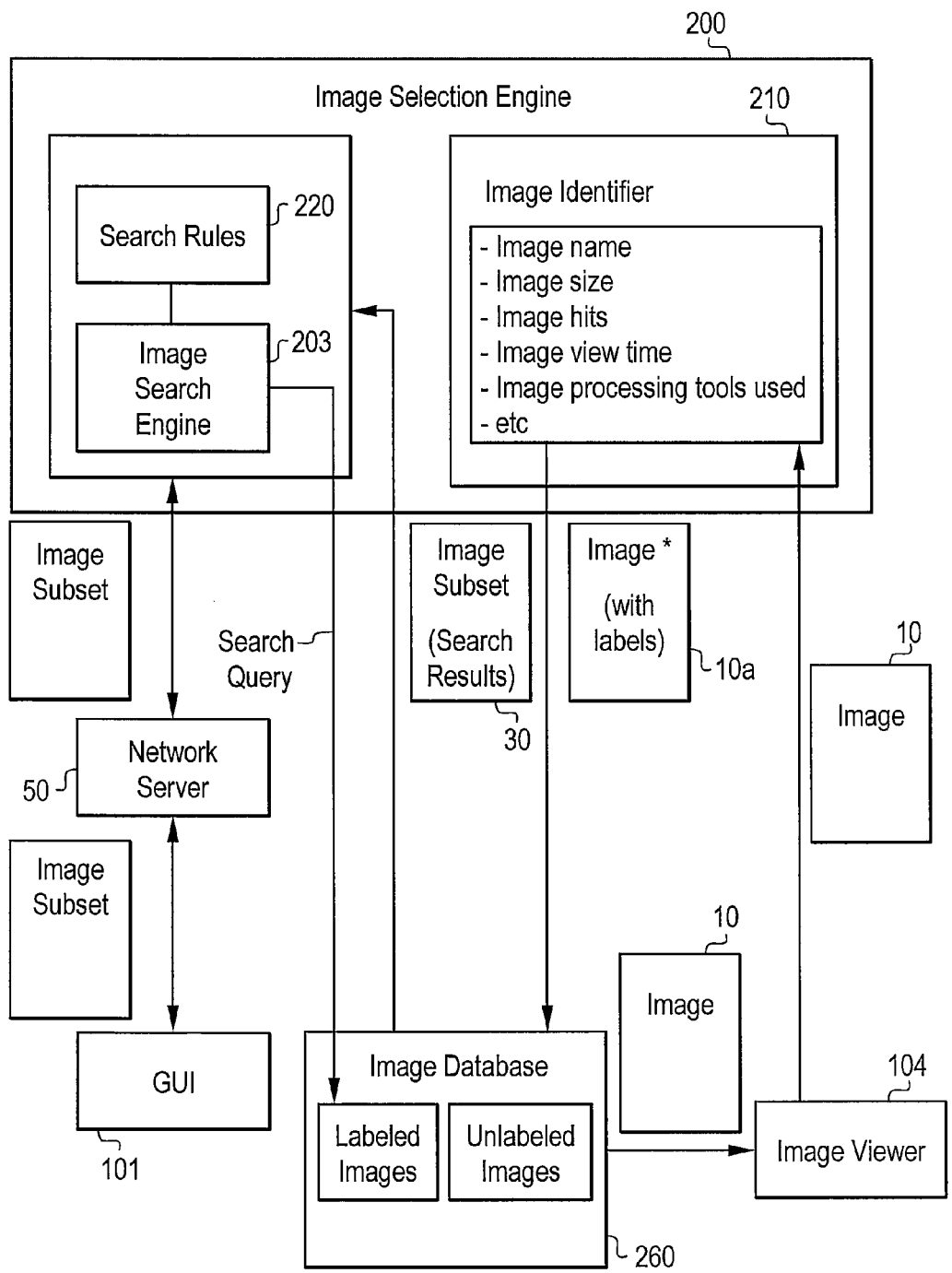
FIG. 3 illustrates a more detailed block diagram of certain components of the teaching file creation system of FIG. 2.

FIG. 3 depicts a block diagram of an exemplary image selection engine in operation with an image viewer and an image database. The image viewer 104 draws an image 10 from the image database so that a user such as a medical practitioner may view the image. In certain embodiments the image viewer 104 may be a GUI, such as GUI 110. An image identifier 210 operates as a component of the image selection engine 200 and records and labels the image 10 based on image information, or data pertaining to the image 10 and the user interaction with the image 10 through the image viewer 104. For example, the image label identifier 210 may record various image information such as the image name, the image size, the image resolution, the number of times the image 10 has been accessed or viewed by the image viewer 104, the GUI 110 or any other system component, the length of time the image 10 was viewed by a user, the image processing tools (e.g., zoom in or out, pan, crop, cut and paste, resize, rotate, highlight, annotate, change window and level settings, change brightness or contrast, etc.) used by the user of the image viewer 104, the name of the images viewed before and after the image 10 was viewed by the image viewer 104.

The image identifier 210 applies an image label to each image 10 as it is viewed by the image viewer 104, and continually updates and indexes the images with labels accordingly as such indexing is applicable. In certain embodiments, the image identifier 210 component of the image selection engine 200 may apply a new image label, or an image tag to the modified image 10a and index the image accordingly in the image database 102.

Working with the image identifier 210 in the image selection engine 200 is an image search engine 230 component. The image search engine 230 is governed by a set of search engine rules 220 and operates to produce the image subset 30. For example, the search engine rules 220 may indicate that the image subset 30 should be composed of the one hundred (100) images viewed the longest by the user. In other words, in certain embodiments, the rules may state that the image search engine 230 should scan the image tags of each image in the database 102 and identify the one hundred images that have been identified by the image identifier 210 as having the longest user viewing times.

In certain embodiments, the rules 220 may indicate that the image search engine 230 should select a certain percentage of images rather than a specific quantity. For example, the rules 220 may dictate the search engine 230 to select the top five percent of images according to the image view time. In certain embodiments the rules 220 may dictate that the image search engine 230 select images without regard to the quantity of images selected. For example, the rules 220 may dictate the search engine 230 to select all images that have had more than five image processing tools applied to it by the user when viewed in the image viewer 104.

In certain embodiments, the rules 220 may consider each of the several image traits tagged to the images by the image identifier 210. For example, the rules may dictate that the image search engine apply an algorithm considering the images based on length of time viewed by the user, number of times the image was viewed, the number of image processing tools applied to the image and the image size.

In certain embodiments the rules 220 may be modified by a user before, during or after an interpretation or a study to account for certain trends or changes in viewing behavior. For example, a user may enter through an interface image search criteria that operate as the rules 220. For example, a practitioner may desire to generate a subset of images relating to brain tumors that have been viewed by a user for periods greater than 60 seconds. The user may enter criteria in the interface that provides an option to sort by image view time, pulling only images with the words "brain" and "tumor" in the label. The image search engine 230 will scan the database 260 in accordance with the rules 220 as determined by the user entered search criteria.

Similarly, a practitioner viewing images relating to skeletal tissue may recognize that many images elected for previous teaching file messages had an image sharpen processing tool applied multiple times, whereas many of the images not selected for the teaching file message did not. The practitioner may therefore select rules 220 that dictate the image search engine 230 to select images for which the practitioner used an image sharpen processing tool more than one time for the image subset 30. These criteria may be based on an observance by the practitioner when studying a teaching file message that a majority or all of the images provided for a brain tumor teaching file message were viewed for longer than 60 seconds.

In certain embodiments, a user may access the image subset 30 via a Graphical User Interface 101 (GUI) via a computer workstation. In certain embodiments, the GUI 101 may be the same device or workstation as the image viewer 104. For example, during the interpretation process a practitioner may view the images from the database 260 through GUI 101, while the image identifier 210 applies labels to the image based on the user interaction with the image via the GUI 101 as it would if the user used image viewer 104.

In certain embodiments, the GUI may be connected to the image subset 30 and, therefore the image selection engine 200 and the image database 260, via a network server 50 that may provide access to the system 100 for multiple user interfaces 101 or workstations. The network server 50 may be any type of known network including a local area network (LAN), a wide area network (WAN), an intranet, or a global network (e.g., the internet). For example, a user may access the image subset via the internet 50 from a home computer with a GUI 101, or from a computer terminal at a hospital.

From the GUI 101, the user may then select images from the image subset 30 for inclusion in the teaching file message. For example, the user may browse through the subset 30 selecting a portion or all of the images for inclusion in the message. Additionally, the user may desire to seek additional images that are not a part of the image selection engine 200 generated image subset 30, and may thus access the image database 260 from the GUI 101 via the network server 50. From the GUI 101, the user may add additional images from the image database 260 to the teaching file if desired.

When the user is satisfied with the teaching file content, the user may direct the system to send the images to a Medical Imaging Resource Center (MIRC) server 400, where the images may be used to automatically create a teaching file that is compliant with the MIRC document schema. MIRC is one implementation of a TCE compliant teaching file receiver to which a teaching file message may be sent, however, the teaching file message could be sent to any teaching file server, or to any system that implements the IHE-TCE Receiver Actor. In certain embodiments, transmission of teaching file images and data from the PACS to the teaching file server will be done using mechanisms that are compliant with the IHE-TCE teaching file profiles.

Because he image selection engine 200 produces the image subset 30, which may comprise only a fraction, for example 1%, of the total images in the study, the practitioner's job is made significantly easier as the time required to search for acceptable images is reduced. Whereas a practitioner would otherwise have to browse through each image, identifying and/or flagging each image suitable for a teaching file message, the image selection engine 200 does a good portion of this work in advance.

Images by themselves rarely offer enough information to provide adequate teaching value. Accordingly, teaching files also contain data fields to accompany the images. The process of generating a teaching file message therefore also requires a user to provide supporting data to accompany the images. Examples of supporting data may include patient data, medical reports, articles or recitations helping to define, explain or describe certain aspects of the medical field. Supporting data may be memos or notes written by the practitioner specifically for the teaching file message of at another time. Supporting data may be in the form of charts, tables or other images that provide history, findings and differential diagnoses, for example, in the field of the subject matter of the teaching file images.

Typically, a practitioner searching for supporting data to accompany images in a medical teaching file message must peruse several healthcare information systems outside the PACS. Each healthcare information system may comprise a plethora of databases, making the search task tiresome, while also reducing the likelihood that the practitioner will have access to all the supporting data necessary to adequately accompany the images.

In certain embodiments, a free text search engine is provided on the PACS, allowing a practitioner to search through a variety of healthcare systems and databases to find the desired supporting data to correspond with the images for the teaching file message. In certain embodiments, the free text search engine is outside of, but in communication with the PACS.

FIG. 2 further depicts a supporting data selection engine 300 connected to the network server 50. In certain embodiments, the supporting data selection engine 300 may be a free text search engine to automatically populate teaching data fields using data retrieved from one or more healthcare information systems 360 based on the patient, study and teaching file field names. In certain embodiments, the supporting data selection engine 300 may interact with the GUI 101, or another interface to accept search criteria, and to display search results.

Figure 4:
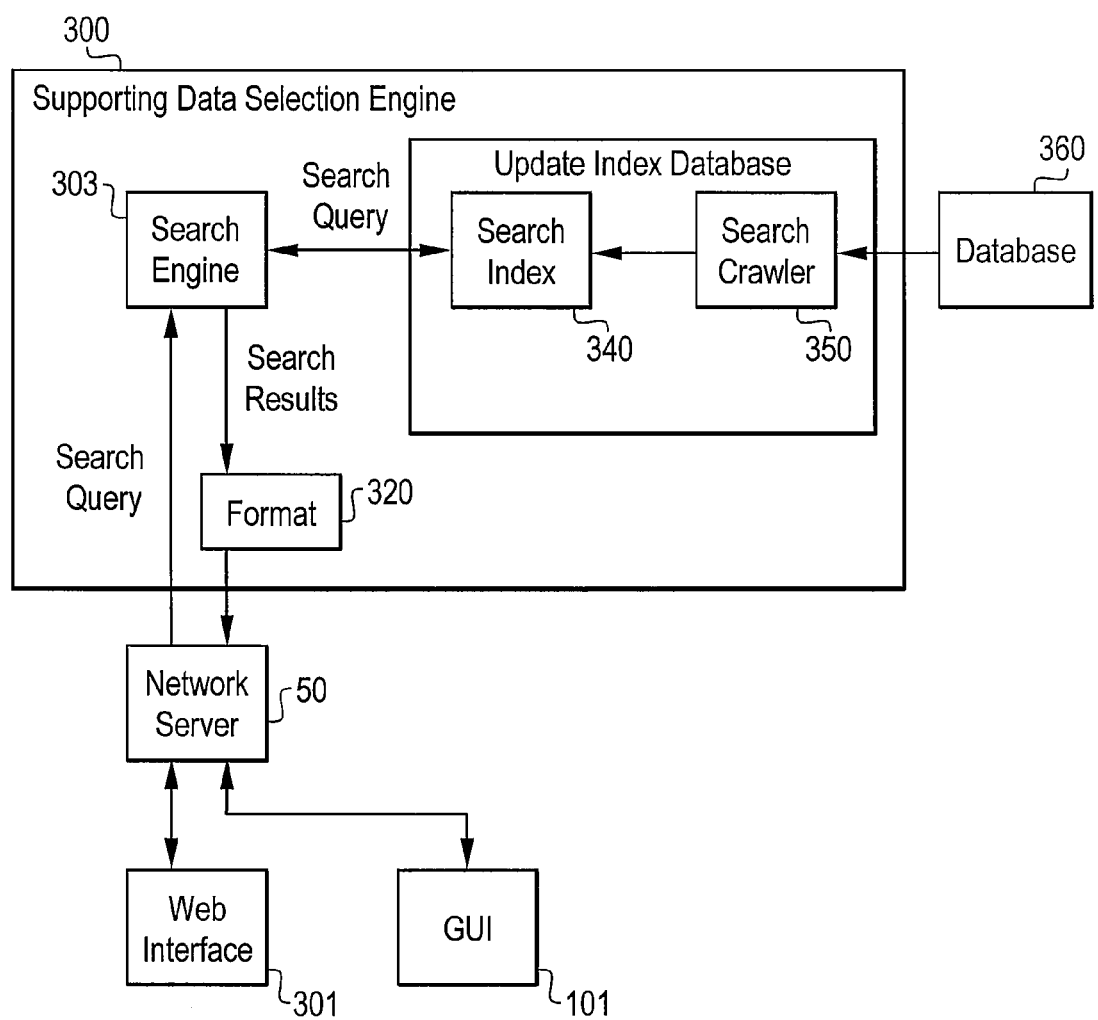
FIG. 4 illustrates a more detailed block diagram of certain components relating to supporting data selection of the teaching file creation system of FIG. 2.

FIG. 4 depicts a block diagram of an exemplary supporting data selection engine in operation with a network, a web interface and a healthcare information system. In certain embodiments a user such as a medical practitioner may access a search via a web interface 301 (which may be similar or identical to GUI 101). One or more search criterion may be entered via the interface 301. In certain embodiments, the interface 301 sends a search query to a search engine 330, which routes (in certain embodiments, with some processing/formatting) the search query to a search index 340. The search index 340 communicates with a search crawler 350 to convey the search query.

The search crawler 350 uses the term(s) of the search query to search a healthcare information system database 360, such as an electronic medical records (EMR) database. In certain embodiments, there may be more than one database 360. In certain embodiments, the database 360 may be a healthcare information system comprising a plurality of databases. Certain embodiments may also provide a connection to multiple healthcare information systems, each system comprising one or more databases.

The search crawler 350 performs a free text search within the database 360, for example. A free or full text search is a search for a match of one or more specified words in the electronic documents of the EMR database 360, for example. The search may be limited by subject matter and/or other criterion, for example. In certain embodiments, the database 360 includes multiple databases spanning multiple departments/facilities, and the crawler 350 searches one or more of these databases based on search terms/parameters.

For example, a free text search may include "CR CHEST", "CT CHEST WITH CONTRAST", "heterogeneous echotexture of the liver", "acute intracranial hemorrhage", etc. Advance searching may include, for example, "Procedure: CHEST & Modality: CT & Referring Physician: AAA & Date Range: From Jan. 2, 2007 to Jun. 6, 2007"; "Procedure: PELVIS & Modality: CT & Comments: osseous lesions & Referring Physician:"; "Procedure: CHEST & Modality: XA|Modality: CT & Comments: coronary artery bypass & Department:Cardiology|Department:Radiology"; etc.

Search results are then provided to the search index 340, which may keep a running track of search results. The search index 340 may be organized using a tree structure, for example. However, a variety of indices may be implemented. The search index 340 is used to collect, organize, parse and store search results for retrieval. Search results are then passed back to the search engine 330. The search engine 330 may then send the results through a formatter 320. The formatter 320 formats the search results for display via the web interface 301. In certain embodiments, the formatter 320 de-identifies certain patient and/or physician identification information from the search results prior to display via the web interface 301. In certain embodiments, results can be categorized to relevance factor and/or other criterion, for example.

Figure 5:
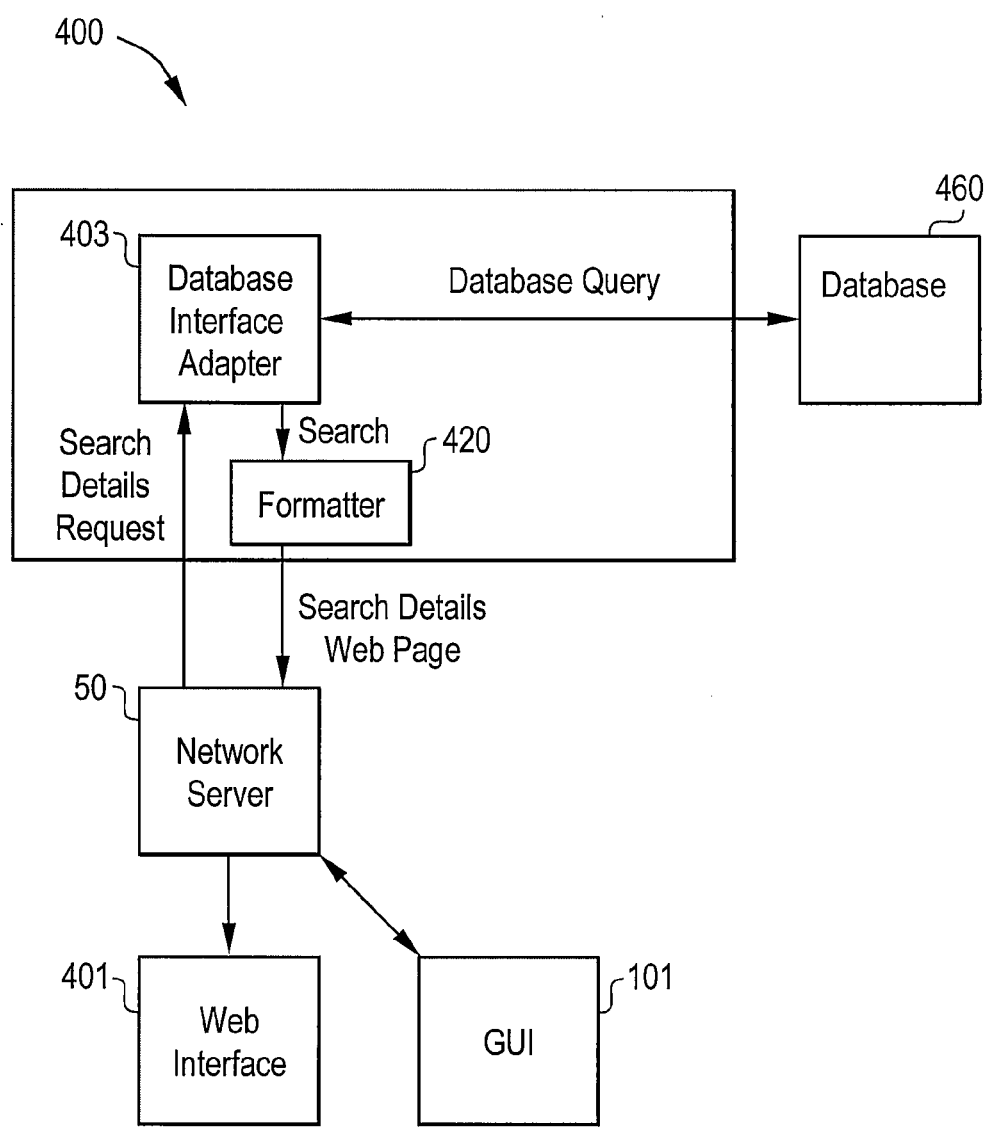
FIG. 5 illustrates a more detailed block diagram of certain components relating to supporting data fetching system of the teaching file creation system of FIG. 2.

As shown in FIG. 5, a user may fetch details of a search via a web interface 401 (which may be the same as or similar to the web interface 301, or GUI 101). The web interface 401 requests data from a database interface adapter 430. The database interface adapter 430 retrieves data from a database 460 (which may be the same as or similar to the database 360). Search details are retrieved from the database 360. The database interface adapter 330 then provides the search details to a formatter 420 (which may be the same as or similar to the formatter 320). The formatter 420 formats the data so that it is appropriate for display via the web interface 301. Formatting may include helping to ensure compliance with the IHE-TCE standards, for example.

Components of systems 300 and 400 may be implemented in software, hardware and/or firmware and may be implemented individually and/or in a variety of combinations.

In certain embodiments, information in medical reports and/or other supporting data documents may be processed to normalize or "scrub" the information according to a particular lexicon and/or grammar. For example, a medical report table, such as a Logician® medical data table, may include one or more observation values from an examining physician or other medical professional. The observation value (e.g., "obs" or "obsvalue") field may be a free-format field, for example. Thus, different physicians may use different language to refer to the same condition. For example, one practitioner may refer to a heart attack while another may refer to an acute myocardial infarction. Terms may be "scrubbed" or parsed and associated with a numeric value and/or "standard" term for a lexicon/grammar.

In certain embodiments, certain identified patient data is extracted and stored centrally in a large data warehouse. During storage, the data may be scrubbed and normalized by mapping terms to a common vocabulary and/or set of rules. For example, if one record refers to a MI and another record refers to a myocardial infarction, both are coded centrally in the database as a myocardial infarct. Thus, a search of records in the database may be executed based on the common vocabulary.

A user may execute a search using one or more terms or criteria for the search. For example, a user may request a pool of medical reports pertaining to patients over the age of 55 with a history of acute myocardial infarction published within the last 2 years from institutions in the Midwest. The terms and/or criteria may already be codified in the database and/or may be codified/normalized upon entry of the search terms by the user, for example. In certain embodiments, a user may select one or more codified terms from a menu or other listing and select one or more predesigned algorithms to search for patients meeting the selected term(s). In certain embodiments, a user may codify additional term(s) and/or create additional rules/search algorithms dynamically, for example. In certain embodiments, a search system accommodates a user's query to codify language used in the query to a standard vocabulary or set of allowed terms. A search having multiple criteria may progress by applying the plurality of criteria in succession to narrow the pool of candidates. Search terms may be matched to electronic medical records and/or other entries in a data warehouse and/or other database, for example.

In certain embodiments, electronic medical record data may be centralized and codified. In certain embodiments, electronic medical record data may be distributed and/or uncodified. In certain embodiments, electronic medical record data may be codified differently in different systems. For example, a local vocabulary may be different from a centralized vocabulary and/or different local healthcare information systems may have different local vocabularies. In certain embodiments, a mapping may exist between a plurality of codifications to allow conversion and searching between the different codification schemes.

Terms or input by a user may be codified according to a diagnostic code such as an ICD-9 (International Classification of Diseases, Ninth Revision) code, ICD-10 code or a CPT (Current Procedure Terminology) code, for example. Alternatively and/or in addition, terms may be codified according to a proprietary terminology or coding schema. For example, an industry standard term such as "acute, upper right extremity pain" may be classified as "acute, upper right arm pain." Certain terms may be classified or replaced by commonly used terms and/or terms appropriate for a particular environment or application, for example. In certain embodiments, a user may select a term, and a master vocabulary table returns relevant terms for use in searching. In certain embodiments, one or more categories may be searched base on a clinical condition or a disease category, for example.

For example, if a user wishes to search for a "CV" (cardiovascular) document or report, the user may select a number of CV conditions from a CV list. For example, a search interface may have clinical conditions listed, such as a person who had a heart attack with complications from diabetes, and the interface may have diagnostic codes listed for selection to search. A user may then search on either or both of the clinical conditions and codes by selecting conditions/codes from a flat or tiered listing or menu and/or by manually entering conditions/codes to select the clinical conditions and/or other criteria to be used to be applied to the database and search.

According to one of the examples above, a user selects the following criteria for searching: age exceeding 55, acute myocardial infarction, within a time frame of 2 years, a certain specified enzyme level or range of levels, and a geographic location of "the Midwest. A search would identify patients in the database over 55 years of age. The search would narrow that group by identifying those patients in the over 55 age group having an acute myocardial infarction within the last two years. Additionally, the search would narrow the group of patients to isolate patients over 55 who have had an acute myocardial infarction in the last two years who reside in the Midwest.

Certain embodiments provide free text searching capability within electronic medical records with automatic de-identification of patient/physician information. Additionally, certain embodiments provide multiple searching capabilities within EMR databases. Searching capabilities may include searching an entire site/database for user-entered search criteria. Search capabilities may include searching a specific department, such as radiology, cardiology, pathology, etc. Search capabilities may include searching images and/or locating similar images from search results. While these capabilities are simply illustrative examples, a variety of other search capabilities may be implemented according to certain embodiments of the present invention.

In certain embodiments, a web interface can be used to access the search capabilities. Additionally, application program interfaces (APIs) can be provided for certain research capabilities. For example, APIs can be provided for finding statistical information such as a number of diagnoses for a specific disease in a specific demography, a number of diagnoses for a patient of a specific disease, etc. A search crawler may be used with a variety of information systems, such as a RIS, PACS, CVIS, LIS, etc.

Figure 6:
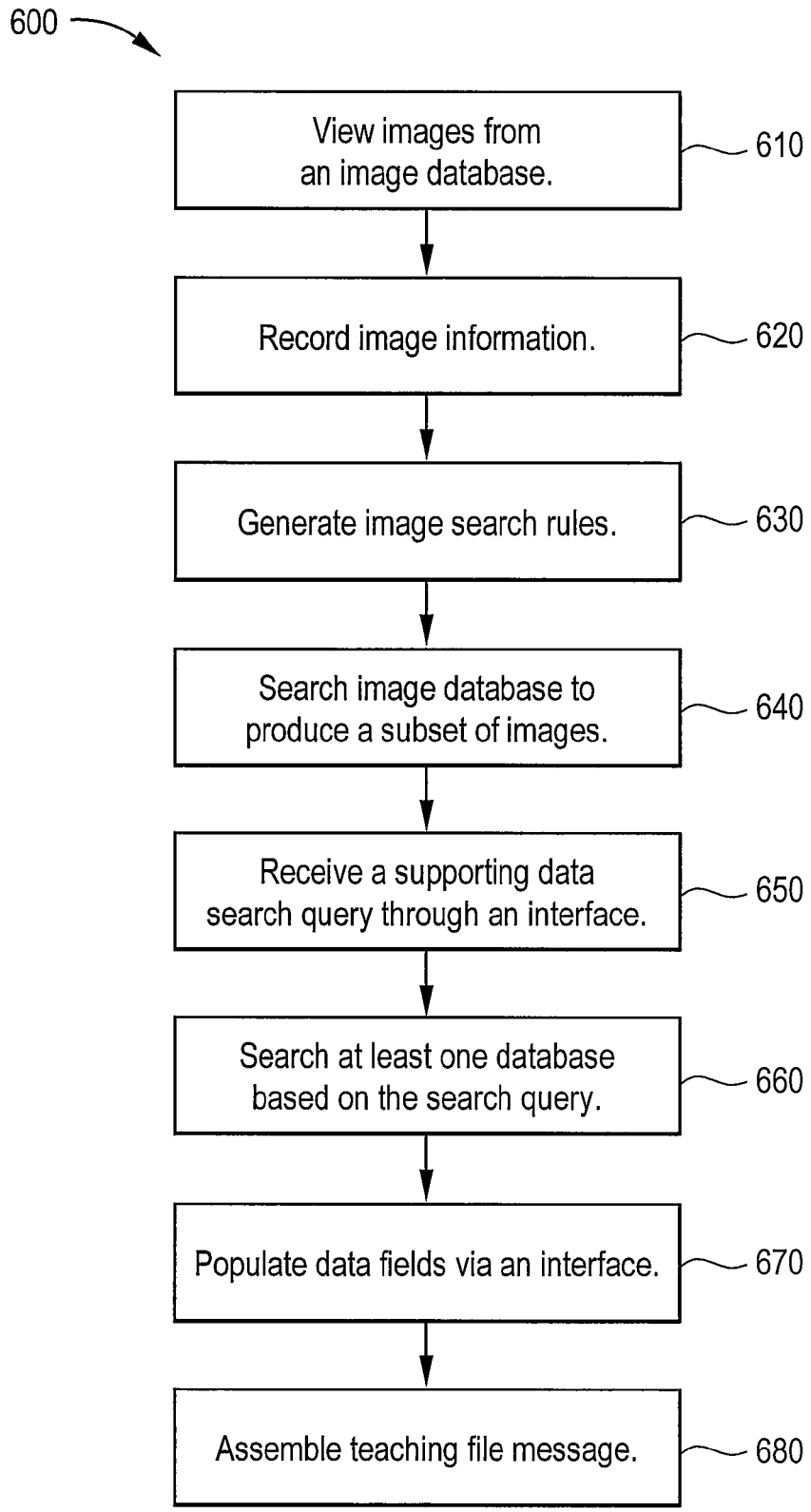
FIG. 6 illustrates a flow diagram demonstrating a method for automatically generating a teaching file.

Certain embodiments provide a method for generating a teaching file message using a user interface. FIG. 6 illustrates a method 600 for generating a teaching file message in accordance with an embodiment of the present invention. At step 610, a user, for example, a medical practitioner views images from an image database. In certain embodiments a user may view images as they are recorded from an image recorder, such as a radiology scanner. In certain embodiments a user may browse through a series of images from a particular study, or a patient in a database.

At step 620, information pertaining to the image viewed in step 610 is recorded. In certain embodiments, an image selection engine records image information, and provides a label to each image based on the image information in the image database. In certain embodiments, the image information applied to each image pertains to user interactions with the image. For example, information pertaining to image hits (number of times viewed), image viewing time, image processing tools used is applied as a label to the image. In certain embodiments, images that have not been viewed may have a label indicating that the image has not been viewed. In certain embodiments images may be categorized based on the image label. For example, images may be categorized as images viewed and images yet to be viewed. Additionally, images may be classified as images that had image processing tools applied while viewing and images that had no processing tools applied.

At step 630, image search rules are generated. In certain embodiments the search rules may be pre-established based on certain user tendencies. In certain embodiments a program may continually update the search rules based on user behavioral patterns. For example, a program may recognize that a certain type of image is likely to be included in a teaching file message when the image has been viewed for longer than 60 seconds by a user. Accordingly, in the above example, rules may provide that the search obtain all images that have been labeled as having been viewed longer than 60 seconds. In certain embodiments a user may modify the image search rules, for example, through the use of search queries. For example, through a user interface a user may submit a query to obtain all images that are labeled as having been viewed for longer than 60 seconds.

At step 640, a subset of images is generated. In certain embodiments the image subset may be a percentage of the total number of images viewed by the user. For example, a particular user may view each of one thousand images pertaining to a particular study. In the above example, the subset of images may include 50 images that are determined by the rules generated in 630 to likely be included in a teaching file message. The number of images in the subset may be substantially less than the total number of images considered in order to make the image selection process for teaching file message generation more efficient.

At step 650, a user interface is provided to receive supporting data search queries and transmit the queries to a search engine. In certain embodiments a user interface is provided to accept user inputted search criteria. For example, a user such as a medical practitioner may enter a search query for medical reports pertaining to lung cancer, published in the past six months.

At step 660, a search engine performs a search within at least one database based on the search criteria provided in step 650. In certain embodiments, a search engine performs a free or full text search within said database(s). The search may be limited by subject matter and/or other criterion, for example. For example, where the search criteria are defined as medical reports pertaining to lung cancer, published in the past six months (as in the example described above) the search engine may search through various systems and databases obtaining all medical reports that contain the words "lung cancer" in the title, and that are identified as having been published within six months of the search date.

At step 670 the search results generated in step 660 are populated via the user interface. In certain embodiments, the entire list of search results are produced via the user interface. Alternatively, in certain embodiments, particularly where the results of the search of step 660 are abundant, only a portion of the search results are populated on the user interface. In certain embodiments, the search results are populated based on the relationship of the search results to the search criteria. For example, in the above example, the first listed results may be those documents that contain the most references of the term "lung cancer." Alternatively, the list may be populated based on the publication dates of the medical reports, with the most recently published documents listed first.

At step 680, the user then selects the images and the supporting data to be included in the teaching file message. In certain embodiments, the user may select all images from the image subset and all supporting data populated by the search. The user may also elect, however, to select only a portion of the images and supporting data for the file. In this step the user may browse the image subset and the populated list of supporting data references selecting only a small portion to be included in the teaching file message. For example, a user may wish to generate only a small but concise teaching file and may therefore elect only one or two images and one or two supporting data references for inclusion in the teaching file message.

Certain embodiments provide an assisted means for a user to generate a teaching file message. The described embodiments relieve users such as medical practitioners from having to manually select and retrieve images and data to be included in a teaching file during the interpretation process. Certain embodiments relieve users of the burden of remembering which images must be included in the teaching file message. Certain embodiments relieve the users of the burden of having to browse multiple healthcare information systems for supporting data.

Those skilled in the art will appreciate that the embodiments disclosed herein may be applied to the formation of any clinical system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A system operating on a computer based Picture Archiving and Communication System (PACS) for generating a medical teaching file message, said system comprising:
   an image identifier providing a continuously updated and indexed image label to each medical image in a group of medical images within an image database based at least in part upon image information contained in a PACS;
   a rule based image selection search engine residing on the PACS searching the indexed image labels of said medical images within said image database based on a set of selection rules input into the PACS by a user, and generating a subset of medical images from said group of medical images based upon said selection rules;
   an interface workstation configured to accept search criteria, display search results and display said medical images;
   a supporting data selection search engine residing on the PACS accepting a free text search query for medical teaching file supporting data in the field of the subject matter of the medical images to accompany said subset of medical images from said interface workstation, said free text search query for said supporting data based on search criteria entered via said interface workstation, said search engine communicating with a search crawler; and
   said search crawler searching at least one healthcare information system's databases outside of the PACS for said medical teaching file supporting data in the field of the subject matter of the medical images based on the free text search query entered by the user via said interface workstation, said healthcare information system's databases including at least alphanumeric data and image data, said supporting data search engine providing said medical teaching file supporting data in the field of the subject matter of the medical images search results, said search crawler searching both the alphanumeric and the image data based on said free text search query entered by the user via said interface workstation,
   wherein said image search engine and said supporting data selection search engine populate said interface with the images from said image subset and said medical teaching file supporting data search results via said interface, allowing the user to select medical images and supporting data in the field of the subject matter of the medical images for inclusion in a medical teaching file message, which is assembled and transmitted to a teaching file server for storage.

2. The system operating on a computer based Picture Archiving and Communication System (PACS) for generating a medical teaching file message of claim 1, further comprising a graphical user interface image viewer for accessing, viewing and editing said medical images from said image database.

3. The system operating on a computer based Picture Archiving and Communication System (PACS) for generating a medical teaching file message of claim 2, wherein said image identifier provides a label that is based at least in part upon a user's interaction with said medical image via said graphical user interface image viewer.

4. The system operating on a computer based a Picture Archiving and Communication System (PACS) for generating a medical teaching file message of claim 1, wherein the interface workstation comprises a web interface.

5. The system operating on a computer based a Picture Archiving and Communication System (PACS) for generating a medical teaching file message of claim 1, wherein said image and supporting data selection engine rules are modifiable by a user via said interface workstation.

6. The system of claim 1, further comprising a formatter for formatting the search results for display via the interface workstation.

7. The system of claim 1, wherein a teaching file message comprising the images from said image subset and said supporting data search results is automatically generated and transmitted to a teaching filed server.

8. A computer implemented method for automatically generating a teaching file message on a Picture Archiving and Communication System (PACS) during a medical interpretation process by a user comprising the following steps:
   continuously updating, indexing and recording image label information in a PACS for each image viewed in the PACS during the medical interpretation process by a user;
   searching, by an image selection search engine residing on the PACS, the indexed image labels of said medical images within an image database based on a set of image search rules input into the PACS by the user;
   generating a subset of the images viewed in the PACS during the medical interpretation process by the user according to said image search rules input into the PACS by the user;
   automatically receiving a medical teaching file supporting data free text search query of at least one healthcare information system's databases outside of the PACS by a user through an interface workstation based on one or more free text search terms, said databases including at least alphanumeric data and image data, said supporting data search engine providing said medical teaching file supporting data in the field of the subject matter of the medical images search results based on said search, said search engine communicating with a search crawler;
   crawling initiated by a user, by said search crawler, of the one or more databases associated with one or more healthcare information systems outside of the PACS to identify medical teaching file supporting data in the field of the subject matter of the medical images to accompany said subset of medical images, said search crawler searching both the alphanumeric and the image data based on said free text search query entered by the user via said interface workstation;

populating an interface workstation with said image subset and said supporting data;

selecting images from said image file subset and said medical teaching file supporting data in the field of the subject matter of the medical images from said search query by the user to be included in a teaching file message; and assembling said teaching file message via said interface workstation and transmitting said message to a teaching file server for storage.

9. The method of claim 8, further comprising the step of formatting by said user said supporting data based on said search query as search results for output to said-user on said interface workstation.

10. The method of claim 8, wherein said image search rules are based upon an image search query entered by said user via said user interface workstation.

* * * * *